United States Patent [19]

Regnier et al.

[11] 3,954,765

[45] May 4, 1976

[54] PIPERAZINES DERIVATIVES

[75] Inventors: Gilbert Regnier, Chatenay-Malabry; Roger Canevari, Villebon-sur-Yvette; Michel Laubie, Vaucresson; Jean-Claude Poignant, Bures-sur-Yvette, all of France

[73] Assignee: Science-Union et Cie, France

[22] Filed: Oct. 7, 1974

[21] Appl. No.: 512,461

[30] Foreign Application Priority Data

Oct. 30, 1973 United Kingdom............... 50309/73

[52] U.S. Cl............................. 260/268 BC; 424/250
[51] Int. Cl.².......................................... C07D 295/12
[58] Field of Search ............... 260/268 BC; 424/250

[56] References Cited
UNITED STATES PATENTS 3,808,212   4/1974   Renth et al................... 260/268 BC

OTHER PUBLICATIONS

E. Merck A.G., Chemical Abstracts, Vol. 66, p. 2587u, (1967).
Burger, Medicinal Chemistry, 3rd Ed., pp. 636 and 638 Part I and p. 1588 Part II.

*Primary Examiner*—Joseph A. Narcavage
*Assistant Examiner*—Jose Tovar
*Attorney, Agent, or Firm*—Gordon W. Hueschen

[57] ABSTRACT

Piperazine derivatives of the formula:

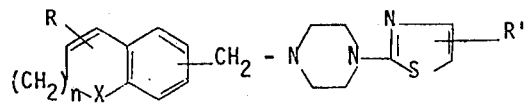

wherein $n$ is 0 or 1, X is oxygen or sulfur, R and R', which are the same or different, are hydrogen or lower alkyl and:

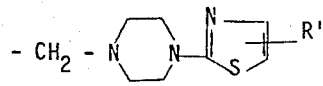

is always bonded to the benzene ring.

These compounds are used as medicine especially in the treatment of peripheral vascular disorders, Parkinson's disease, hypertension and pain.

15 Claims, No Drawings

PIPERAZINES DERIVATIVES

The present invention provides piperazine derivatives of the general formula I:

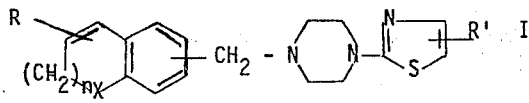

and acid addition salts, especially physiologically tolerable acid addition salts thereof, wherein:
- $n$ is selected from 0 and 1,
- $x$ is selected from the group consisting of an oxygen atom and a sulfur atom,
- R and R', which are the same or different, are each selected from the group consisting of a hydrogen atom and lower alkyl radicals having from 1 to 5 carbon atoms inclusive, and the group:

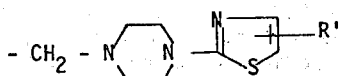

is always bonded to the benzene ring in the group:

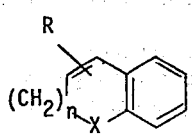

Though all the compounds of the present invention possess valuable pharmacological properties, the compounds of the general formula I, wherein $n$ is 0, are particularly interesting due to their pharmacological behaviour and among them those for which X is sulfur are the preferred compounds.

The compounds of the general formula I are new and they were prepared according to the following processes which are included in the present invention.

The present invention provides a process for preparing a compound of the general formula I which comprises condensing a halo compound of the general formula II:

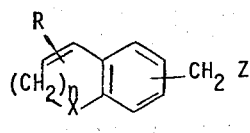

in which $n$, R and X have the meanings given above, Z represents a chlorine or bromine atom, and —CH₂ Z is always bonded to the benzene ring, with a N-mono substituted piperazine of the general formula III:

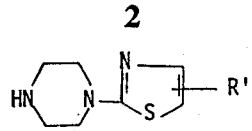

in which R' has the meanings given above.

The present invention also provides a process for preparing a compound of the general formula I which comprises condensing a halo compound of the general formula IV:

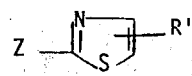

in which R' and Z have the meanings given above with a N-monosubstituted piperazine of the general formula V:

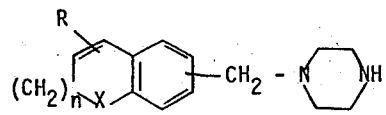

in which $n$, X and R have the meanings given above, and

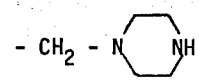

is always bonded to the benzene ring.

The above processes according to the present invention are advantageously carried out in solution in a polar solvent, for example an alcohol having a high boiling point, for example, butanol or pentanol or, preferably an aliphatic amide, for example, dimethylformamide or dimethylacetamide, or in a non-polar solvent for example on aromatic hydrocarbon, for example toluene or xylene. It is advantageous to carry out the reactions at a temperature of from 25° to 140°C in the presence of an acceptor for the hydrogen halide formed in the course of the reaction. As acceptors there may be mentioned, for example alkali metal or alkaline-earth metal salts of carbonic acid, for example sodium or potassium bicarbonate or carbonate or calcium carbonate and tertiary organic bases, for exampel dimethylamine, pyridine or triethylamine; if desired, there may be used instead of a separate acid acceptor, an excess of the mono-substituted piperazine of the formula III or V, the excess acting as an acid acceptor.

The present invention provides a further process for preparing a compound of the general formula I which comprises submitting a mixture of an aldehyde of the general formula VI:

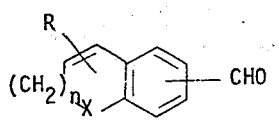 VI

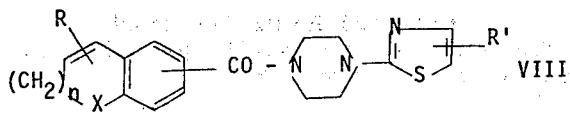 VIII in which n, X and R have the meanings given above, and the —CHO group is always bonded to the benzene ring, and a N-monosubstituted piperazine of the general formula III given above, to an alkylating reduction. This alkylating reduction may be performed with hydrogen at a pressure ≤ 5 atmospheres, in the presence of a small quantity of palladium on charcoal, in a slightly polar aprotic solvent, for example, ethyl acetate or toluene; the use of a hydrogen pressure ≤ 5 atmospheres allows efficient control of the quantity of hydrogen which is absorbed in order to minimize concomitant hydrogenolysis of the:

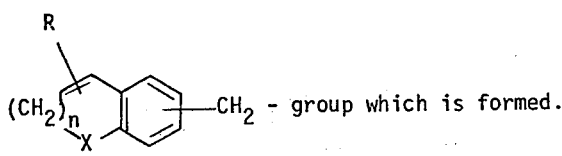 - group which is formed.

Such a process is advantageously carried out by submitting to hydrogenation under a hydrogen pressure ≤ 5 atmospheres, a substantially equimolecular mixture of the compounds of the formulae VI and III, in solution in ethyl acetate, in the presence of a quantity of palladium on charcoal such that the weight of palladium is from 0.15 to 0.2 % of the total weight of the reactants of the formulae III and VI, at a temperature within the range of from 50° to 80° C.

The alkylating reduction of compounds III and VI may also be carried out with a reducing agent such as formic acid in excess. Such a reaction is performed by heating to the boiling temperature a stoichiometric mixture of compounds III and VI in an excess of formic acid until the completion of the release of carbon dioxide.

The present invention also provides a process for preparing a compound of the general formula I which comprises condensing an acyl chloride of the general formula VII:

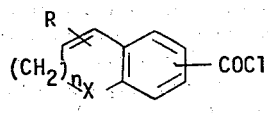 VII wherein n, X and R have the meanings given above and —COCl is always bonded to the benzene ring. with a piperazine of the general formula III given above, then reducing the so-obtained amide of the general formula VIII:

wherein n, X, R and R' have the meanings given above and

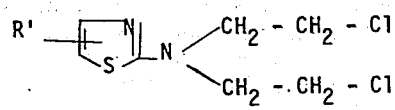

is always bonded to the benzene ring.

One of the most satisfactory way to carry out such a process consists in condensing the compounds III and VII in a solvent for example in an aromatic hydrocarbon having a low boiling point such, for example, as benzene or toluene or in an aliphatic or cycloaliphatic ether such as tetrahydrofuran or dioxane, at a temperature within the range of from 60° to 120° C, in the presence of an acceptor for the hydrochloric acid formed during the reaction. As acceptors there may be used an excess of the piperazine III or a tertiary amine such for example, as triethylamine, pyridine, or dimethylaniline.

A particularly suitable method for reducing the amide VIII consists in using lithium aluminium hydride, the reduction being performed in a solvent having a low boiling point such for example, as ether or tetrahydrofuran, at a temperature within the range of from 35° to 60°C.

The present invention also provides a process for preparing a compound of the general formula I which comprises condensing a chloro compound of the general formula IX:

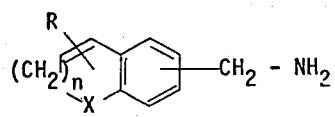 IX wherein R' has the meaning given above, with an amine of the general formula X:

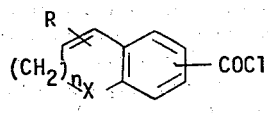 —CH$_2$ — NH$_2$  X wherein n, X and R have the meanings given above and — CH$_2$ — NH$_2$ is always bonded to the benzene ring.

Such a condensation is advantageously carried out in a suitable solvent, at a temperature within the range of from 130° to 150° C, in the presence of an acceptor for the hydrochloric acid, formed during the reaction. As solvents which may be used in such a case there may be especially mentioned the alcohols having 5 or 6 carbon atoms such, for example, as isoamyl alcohol, glycol ethers such, for example, as diglyme, and tertiary amides such, for example, as dimethylformamide and dimethyl acetamide. As an acceptor, there may be used, advantageously an excess of the amine X, or if desired, a tertiary amine such, for example, as pyridine or dimethylaniline.

The chloro compounds of the general formula IX were prepared by chlorinating the corresponding hydroxy compounds of the general formula:

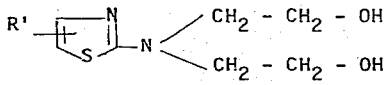

wherein R' has the meanings given above.

The compounds of the general formula I are weak bases, and may be converted by treatment with acids into acid addition salts. As acids which may be used for the formation of these addition salts; there may be mentioned, for example, in the mineral series: hydrochloric, hydrobromic, sulphuric and phosphoric acids, and in the organic series: acetic, propionic, maleic, fumaric, tartaric, citric, oxalic, benzoic and methanesulphonic acids.

The compounds of the formula I may be purified by physical methods, for example by distillation, crystallisation or chromatography, or by chemical methods, for example by the formation of an addition salt followed by crystallisation of the latter and decomposition thereof with an alkaline agent.

The compounds of the general formula I and physiologically tolerable salts thereof possess valuable pharmacological and therapeutic properties, especially peripheral vasodilatory, anti-Parkinson, antihypertensive and analgesic properties. They may, therefore, be used as medicines especially in the treatment of peripheral vascular disorders, Parkinson's disease, hypertension and pain.

Their toxicity is low and their $LD_{50}$ determined in mice is higher than 200 mg/kg by intraperitoneal route.

Their neuroleptic properties were evidenced in the rats and mice by modifications observed on the stereotypy, motility and excitation.

In mice, at the dose of 100 mg/kg IP there were observed a decrease of motility and tonus.

The scores of central nervous system stimulation or stereotypy were determined in the rats according to the method of Quinton and Haliwell, Nature 200, 178 (1963). Scores of up to 255 for 3 hours were observed with doses of 20 to 80 mg/kg IP.

The present invention also provides pharmaceutical compositions which contains a compound of the general formula I or a physiologically tolerable salt thereof in admixture or conjunction with a pharmaceutically suitable carrier, such for example, as distilled water, glucose, lactose, starch, talc, magnesium stearate, ethyl cellulose or cocoa butter.

The so-obtained pharmaceutical compositions are advantageously in unit dosage form and may contain from 10 to 400 mg of the active ingredient.

These pharmaceutical compositions may be in form of tablets, dragees, capsules, suppositories or injectable or drinkable solutions and may be administered by oral, rectal or parenteral route at a dose of 10 to 400 mg, 1 to 5 times a day.

The following examples illustrate the invention, the melting points being determined in a capillary tube.

EXAMPLE 1

1-(5-benzo [b] thienylmethyl)-4-(2-thiazolyl) piperazine

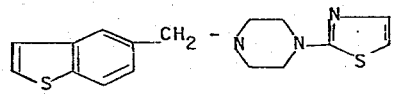

First method:

A solution of 8.6 g (0.0506 mole) of 1-(2-thiazolyl) piperazine and 5.75 g (0.0253 mole) of 5-bromomethyl benzo [b] thiophene (MP 37° C) in 145 ml of anhydrous toluene containing 5 ml of dimethylformamide was stirred at 25° for 24 hours.

At the completion of the reaction, the thiazolyl piperazine hydrobromide which had formed was filtered off and the solvent was evaporated from the filtrate under reduced pressure. There were obtained 10 g of a yellow oil which was treated with 50 ml of a 2N hydrochloric acid solution. The acid solution was washed with ether and the base was salted out with an excess of potassium carbonate. There were obtained 6 g of a crude crystallized product, which was recrystallized in 20 ml of ethanol to give 5 g of 1-(5-benzo [b] thienylmethyl)-4-(2-thiazolyl) piperazine as beige crystals melting at 80°–82° C.

Second method:

A solution of 12 g (0.1 mole) of 2-chlorathiazole and 23.2 g (0.1 mole) of 1-(5-benzo [b] thienylmethyl) piperazine in 150 ml of dimethylformamide in the presence of 28 g of dried potassium carbonate was boiled for 9 hours. After completion of the reaction the salt which had formed was filtered off and the solvent was evaporated under reduced pressure.

The crude residue was washed several times with water, dried and then recrystallized in 120 ml of ethanol. There were obtained 25 g of 1-(5-benzo [b] thienylmethyl-4(2-thiazolyl) piperazine as beige crystals melting at 80°–82° C.

Third method:

A solution of 8.1 g (0.05 mole) of 5-formyl-benzo [b] thiophene and 8.45 g (0.05 mole) of 1-(2-thiazolyl) piperazine in 400 ml of ethyl acetate was hydrogenized under a hydrogen pressure ≤ 5 atmosphere, in the presence of 5 g of palladised charcoal (5 % Pd), at a temperature of 80° C.

When the theoretical amount of hydrogen had been absorbed, the catalyst was filtered off and the filtrate was extracted several times with a normal methane-sulphonic acid solution. The acid solution was washed several times with ether and the base was salted out with an excess of potassium carbonate then extracted with chloroform. The solvent was evaporated under reduced pressure and the semicrystalline residue was recrystallized in ethanol.

There were obtained 7.5 g of beige crystals of 1-(5-benzo [b] thienylmethyl)-4-(2-thiazolyl) piperazine melting at 80°–82° C.

This alkylating reduction was also carried out as follows:

A mixture of 8.1 g (0.05 mole) of 5-formyl-benzo [b] thiophene and 8.45 g (0.05 mole) of 1-(2-thiazolyl) piperazine in 100 ml of formic acid was boiled for 3 hours. When the release of carbon ddioxide was stopped, the solvent was evaporated under a reduced pressure and the residue was dissolved in 200 ml of water. After several extractions with ether, the aqueous solution was rendered alkaline with $K_2CO_3$. The so-obtained crude crystallized base was recrystallized in 25 ml of ethanol. There were obtained 7 g of beige crystals of 1-(5-benzo [b] thienylmethyl)-4-(2-thiazolyl)piperazine melting at 80°–82° C.

Fourth method:

A solution of 8.2 g of 1-(5-benzo [b] thienyl carbonyl)-4-(2-thiazolyl)piperazine (MP 152° C) and 120 ml of anhydrous tetrahydrofuran was heated, at the boiling temperature, in the presence of 1.8 g of lithium aluminium hydride, for 18 hours. Then the mixture was cooled and there were successively added 2 ml of water, 2 ml of a 2N sodium hydroxide solution and 6 ml of water. The so-formed precipitate of alumina was filtered off and the solvent was evaporated under a reduced pressure. The crystallized residue was treated with 50 ml of normal hydrochloric acid. The unsoluble matter was filtered off; the filtrate was rendered alkaline with an excess of potassium carbonate then extracted with ether. After evaporation of ether the crystalline residue was taken up with boiling ethanol. There were finally obtained after recrystallization, 5.2 g of beige crystals of 1-(5-benzo [b] thienylmehtyl)-4-(2-thiazolyl) piperazine melting at 80°–82° C.

The starting 1-(5-benzo [b] thienyl carbonyl)-4-(2-thiazolyl) piperazine was prepared by condensing 5-benzo [b] thienyl carboxylic acid chloride with 1-(2-thiazolyl) piperazine, in anhydrous tetrahydrofuran, at the boiling temperature in the presence of triethylamine.

Fifth method:

A mixture of 11.2 g of 2-[bis- ($\beta$-chloroethyl) amino] thiazole, 24.5 g of 5-aminomethyl benzo [b]thiophene and 300 ml of diglyme was heated at 150° C for 12 hours. Then the solvent was eliminated under a reduced pressure and the viscous residue was taken up with 300 ml of water and 300 ml of benzene. After decantation, the aqueous phase was extracted with benzene. The organic phase was then extracted several times with a normal solution of methane sulfonic acid and the acid portion was then rendered alkaline with an excess of potassium carbonate. The so-obtained oily base was extracted with ether. The etheral layer was dried, then ether was evaporated and the syrupy residue was dissolved in 50 ml of boiling ethanol. There were obtained after crystallization 10.1 g of beige crystals of 1-(5-benzo [b] thienylmethyl)-4-(2-thiazolyl) piperpiperazine melting at 80°–82°C.

EXAMPLES 2 to 7

The following compounds were prepared accoridng to the processes described in example 1.

2. 1-(6-benzo [b]thienylmethyl)-4-(2-thiazolyl)piperazine, MP 98°–100°C, was prepared:
  by condensing 6-chloromethyl benzo [b] thiophene and 1-(2-thiazolyl) piperazine in anhydrous toluene containing dimethyl formamide, at 110° C for 7 hours (yield: 68 %).
  by condensing 2-chlorothiazole and 1-(6-benzo [b] thienylmethyl) piperazine;
  by alkylating reduction of 6-formyl benzo [b] thiophene and 1-(2-thiazolyl) piperazine;
  by condensing 6-benzo [b] thienyl carboxylic acid chloride with 1-(2-thiazolyl) piperazine then reducing the so-obtained 1-(6-benzo [b] thienyl carbonyl)-4-(2-thiazolyl) piperazine; and
  by condensing 2-[bis($\beta$-chloroethyl) amino] thiazole and 6-aminomethyl benzo [b] thiophene.

3. 1-(2-methyl-5-benzo [b] thienyl methyl)-4-(2-thiazolyl) piperazine was prepared:
  by condensing 2-methyl-5- chloromethyl benzo [b] thiophene and 1-(2-thiazolyl) piperazine;
  by condensing 2-chlorothiazole and 1-(2-methyl-5-benzo [b] thienylmethyl) piperazine;
  by alkylating reduction of 2-methyl-5-formyl benzo [b] thiophene and 1-(2-thiazolyl) piperazine;
  by condensing 2-methyl-5-benzo [b] thienyl carboxylic acid chloride with 1-(2-thiazolyl) piperazine, then reducing the so-obtained 1-(2-methyl-5-benzo [b] thienyl carbonyl)-4-(2-thiazolyl) piperazine, and
  by condensing 2- [bis($\beta$-chloroethyl) amino] thiazole and 2-methyl-5-aminomethyl benzo [b] thiophene.

4. 1-(5-benzo [b] thienylmethyl)-4-(4-methyl-2-thiazolyl) piperazine was prepared:
  by condensing 5-chloromethyl benzo [b] thiophene and 1-(4-methyl-2-thiazolyl) piperazine;
  by condensing 4-methyl-2-chlorothiazole and 1-(5-benzo [b] thienylmethyl) piperazine;
  by alkylating reduction of 5-formyl benzo [b] thiophene and 1-(4-methyl-2-thiazolyl piperazine;
  by condensing 5-benzo [b] thienyl carboxylic acid chloride with 1-(4-methyl-2-thiazolyl) piperazine then reducing the so-obtained 1-(5-benzo [b] thienyl carbonyl) 4-(4-methyl-2-thiazolyl) piperazine; and
  by condensing 4-methyl-2- [bis ($\beta$-chlorethyl) amino] thiazole and 5-aminomethyl benzo [b] thiophene.

5. 1-(2H-thiachromen-6-yl methyl)-4-(2-thiazolyl) piperazine was prepared:
  by condensing 6-chloromethyl-2H-thiachromene and 1-(2-thiazolyl) piperazine;
  by condensing 2-chlorothiazole and 1-(2H-thiachromen-6-yl methyl) piperazine;
  by alkylating reduction fo 6-formyl -2H-thiachromene and 1-(2-thiazolyl) piperazine;
  by condensing 2H-thiachromen-6-yl carboxylic acid chloride with 1-(2-thiazolyl) piperazine, then reducing the so-obtained 1-(2H-thiachromen-6-yl carbonyl)-4-(2-thiazolyl) piperazine; and
  by condensing 2- [bis-($\beta$-chloroethyl) amino] thiazole and 6-aminomethyl-2H-thiachromene.

6. 1-(5-benzo [b] furylmethyl)-4-(2-thiazolyl) piperazine was prepared:
  by condensing 5-chloromethyl benzo [b] furan and 1-(2-thiazolyl) piperazine;
  by condensing 2-chlorothiazole and 1-(5-benzo [b] furylmethyl) piperazine;

by alkylating reduction of 5-formyl benzo [b] furan and 1-(2-thiazolyl) piperazine;

by condensing 5-benzo [b] furyl carboxylic acid chloride with 1-(2-thiazolyl) piperazine then reducing the so-obtained 1-(5-benzo [b] furyl carbonyl)-4-(2-thiazolyl) piperazine; and by condensing 2- [bis-(β-chloroethyl) amino] thiazole and 5-aminometheyl benzo [b] furan.

7. 1-(2H-chromen-6-yl methyl)-4-(2-thiazolyl) piperazine was prepared:

by condensing 6-chloromethyl-2-H-chromene and 1-(2-thiazolyl) piperazine;

by condensing 2-chlorothiazole and 1-(2H-chromen-6-yl methyl) piperazine;

by alkylating reduction of 6-formyl-2H-chromene and 1-(2-thiazolyl) piperazine;

by condensing 2H-chromen-6-yl carboxylic acid chloride with 1-(2-thiazolyl) piperazine, then reducing the so-obtained 1-(2H-chromen-6-yl carbonyl)-4-(2-thiazolyl) piperazine, and by condensing 2- [bis-(β-chloroethyl) amino] thiazole and 6-amino methyl-2H-chromene.

We claim:

1. A compound selected from the group consisting of:

A. compounds of the formula I:

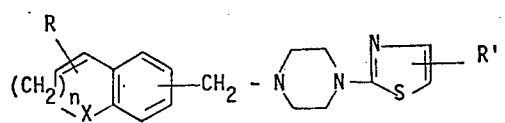

wherein:
n is selected from 0 and 1,
X is selected from the group consisting of oxygen and sulfur,
R and R', which are the same or different, are each selected from the group consisting of hydrogen and alkyl having from 1 to 5 carbon atoms inclusive, and
the group:

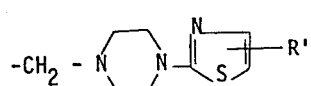

is always bonded to the benzene ring in the group:

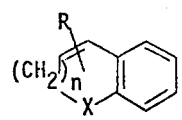

and,

B. Physiologically tolerable acid addition salts thereof.

2. A compound of claim 1 of the formula I':

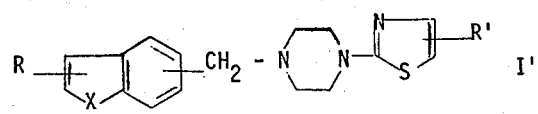

wherein X, R and R' have the meanings given in claim 1 and physiologically tolerable acid addition salts thereof.

3. A compound of claim 1 of the formula I":

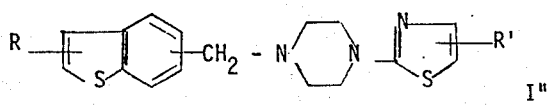

wherein R and R' have the meanings given in claim 1 and physiologically tolerable acid addition salts thereof.

4. A compound of claim 1 which is 1-(5-benzo [b] thienylmethyl)-4-(2-thiazolyl) piperazine.

5. A compound of claim 1 which is 1-(6-benzo [b] thienylmethyl)-4-(2-thiazolyl) piperazine.

6. A compound of claim 1 which is 1-(5-benzo [b] furylmethyl)-4-(2-thiazolyl) piperazine.

7. A compound of claim 1 which is 1-(2H-chromen-6-yl methyl)-4-(2-thiazolyl) piperazine.

8. A pharmaceutical composition consisting essentially of a compound of claim 1 in an amount of 10 to 400 mg, together with a suitable pharmaceutical carrier.

9. A method of treating a living animal body afflicted with peripheral vascular disorders, Parkinson's disease, hypertension or pain, comprising the step of administering an amount of a compound of claim 1 which is effective for the alleviation of the said condition.

10. A compound of claim 1, in which R and R' are hydrogen, and physiologically tolerable acid addition salts thereof.

11. A compound of claim 1, in which alkyl having from 1 to 5 carbon atoms inclusive, is methyl, and physiologically tolerable acid addition salts thereof.

12. A compound of claim 2, in which R and R' are hydrogen, and physiologically tolerable acid addition salts thereof.

13. A compound of claim 2, in which alkyl having from 1 to 5 carbon atoms inclusive, is methyl, and physiologically tolerable acid addition salts thereof.

14. A compound of claim 3, in which R and R' are hydrogen, and physiologically tolerable acid addition salts thereof.

15. A compound of claim 3, in which alkyl having from 1 to 5 carbon atoms inclusive, is methyl, and physiologically tolerable acid addition salts thereof.

* * * * *